United States Patent
Rajala et al.

[11] Patent Number: 5,552,007
[45] Date of Patent: Sep. 3, 1996

[54] CONVEYING CONTINOUS WEB HAVING CROSS-DIRECTION TENSION

[75] Inventors: Gregory J. Rajala, Neenah; Gerald L. Rabe, Appleton; Paul M. Niemi, Neenah; Donald J. Holewski, Greenville, all of Wis.

[73] Assignee: Kimberly-Clark Corporation, Neenah, Wis.

[21] Appl. No.: 382,109

[22] Filed: Jan. 31, 1995

[51] Int. Cl.⁶ .............................. B32B 31/06; A61F 13/15
[52] U.S. Cl. .......................... 156/164; 156/160; 156/163; 156/229; 156/494; 156/496
[58] Field of Search ................................... 156/160, 163, 156/164, 229, 494, 495, 496

[56] References Cited

U.S. PATENT DOCUMENTS

| | | |
|---|---|---|
| 3,644,157 | 2/1972 | Draper ................................... 156/160 |
| 4,364,787 | 12/1982 | Radzins . |
| 4,642,150 | 2/1987 | Stemmler . |
| 4,735,673 | 4/1988 | Piron . |
| 4,925,520 | 5/1990 | Beaudoin et al. . |
| 5,000,806 | 3/1991 | Merkatoris et al. ..................... 156/164 |
| 5,296,080 | 3/1994 | Merkatoris et al. ..................... 156/496 |

FOREIGN PATENT DOCUMENTS 126618  1/1948  Australia ................................ 156/164

OTHER PUBLICATIONS

Technical Data Sheet, Plasma Coatings, Inc. 900 Release/Transaction Series.

Primary Examiner—Jeff H. Aftergut
Attorney, Agent, or Firm—Donald L. Traut; Mark L. Davis

[57] ABSTRACT

This invention pertains to handling a continuous web in a continuous processing operation wherein the web incorporates therein one or more stretched elastic-type elements having retractive forces active in the cross-machine direction, and limiting shrinkage of the web in the cross-machine direction to no more than about 5%. Shrinkage in the width dimension is controlled using methods including transporting the web on a sequence of rolls having on their outer working surfaces protuberances which interact with edges of openings in the web, inhibiting lateral movement of elements defining the edges of the openings, and thereby stabilizing the web in the width dimension.

67 Claims, 5 Drawing Sheets

CONVEYING CONTINOUS WEB HAVING CROSS-DIRECTION TENSION

FIELD OF THE INVENTION

This invention relates to handling a continuous web in a continuous processing operation wherein the web incorporates therein one or more elastic-type elements having retractive forces active in the cross-machine direction, while avoiding reduction of the width of the web due to such retractive forces.

BACKGROUND OF THE INVENTION

It is known to incorporate elastic-type elements into a continuous web in a continuous processing operation wherein the elastic elements extend in the longitudinal, or machine, direction in the web. Such elastic elements may be incorporated in such manner that the elements are in a stretched state, having retractive forces active in the longitudinal, or machine, direction, during the continuous processing of the web. So long as such retractive forces are confined to the machine direction, the effect of the retractive forces on the registration of the web can be controlled by controlling the tension on the web.

In continuous processing of a substantially endless web, as in the instant invention, it is known to perform a plurality of processing steps on the web in sequence. Typically, it is desired to perform one or more of the processing steps at specific locations in the web, wherein a second step is performed at a particular locus with respect to a first, or previous, step, whereby it is critical to be able to locate, at the work station for performing the second step, the location at the which the previous step was performed. In the art, this is known as being able to "register" the second step with respect to the first step.

A first factor in being able to register a second processing step with respect to a first processing step, is being able to determine the distance, and the direction, that the work locus on the web where the first step was performed, has travelled from the location in the processing apparatus where the first step was performed. Such determination can be divided into four assessment steps.

First, one determines the longitudinal distance, in the machine direction, travelled by the work locus in the web.

Second one determines the width distance, in the cross-machine direction, travelled by the work locus.

Third, one determines shrinkage in the machine direction.

Fourth, one determines shrinkage in the cross-machine direction.

The first and third factors can be measured and controlled using conventional control apparatus and methods to control drive speed and tension in the web. The second factor can be controlled using conventional lateral guide apparatus and methods.

The fourth factor is normally accommodated as a dependent dimension controlled by the amount of tension/tensile stress imparted to the web in the machine direction. Namely, as tensile stress is applied to the web in the machine direction, the amount of strain/stretch in the machine direction produces a dependent amount of shrinkage in the web in the cross-machine direction.

Such accommodation, however, assumes that no retractive-type forces are active in the web in the cross-machine direction. To the extent retractive-type forces are active in the web in the cross-machine direction, absent other controls, the web shrinks in the width (cross-machine) direction in response to such active retractive-type forces, thereby changing the width of the web in the cross-machine direction. In processing operations where it is important to maintain a constant, or nearly constant width in the web, other means are needed to maintain constant the width of the web.

It is known to maintain "the width of the web using a tenter frame, wherein an assemblage of gripping devices grips the opposing edges of the web at closely spaced locations, and travels with the web, thus physically restraining the web against reduction in the width dimension so long as the gripping devices have hold of the edges of the web.

Use of tenter frames have four severe limitations. First, they occupy precious working space adjacent the web being processed such that they may interfere with set-up and/or operation of the processing steps whereby the web is otherwise modified.

Second, tenter frames are relatively complex, expensive mechanical devices.

Third, use of tenter frames is generally limited to straight stretches of the processing line. Namely, tenter frames generally are not used to maintain the width of the web as the web traverses about the circumference of a turning roll or a processing roll in the sequence of steps in the processing line. Yet turning rolls and processing rolls are commonly preferred as efficient rotary devices for performing routine steps on webs being processed.

Fourth, the edges of the web gripped by the tenter frame grippers are generally not subsequently used as part of the finished product, whereby the grippers may make a positive contribution to the amount of waste associated with the manufacturing operation.

Another known method for urging width-dimensional stability on a web under cross-machine direction tension is to process the web on a roll coated with silicone rubber, as taught in, for example U.S. Pat. No. 4,925,520 Beaudoin et al. However, a silicone rubber coating presents a number of limitations related to the characteristics of silicone rubber. For example, silicone rubber on a roll carrying the web cannot provide sufficiently rigid surface against which to perform slitting and like cutting operations.

Thus, it is would be desirable to provide additional methods and apparatus for controlling the dimensional stability of a web in the cross-machine direction wherein the web incorporates therein retractive-type forces active in the cross-machine direction.

It is an object of this invention to provide apparatus and methods for providing cross-machine dimensional stability in a continuous web being processed in a continuous process, the web having stretched elastic-type elements which exhibit retractive-type forces active in the cross-machine direction.

It is a further object to provide such apparatus and methods, including a first rotary transport device, transporting the web, including a first set of protuberances thereon for engaging and holding the web, and transferring the web to a second rotary transport device including a second set of protuberances thereon for engaging and holding the web.

It is a further object to provide such apparatus and methods wherein the first and second rotary transport devices have outer working surfaces, carrying the web, which outer working surfaces are aligned with each other across the entire width of the web.

It is yet another object to provide such apparatus and methods wherein the composition of one or more of the outer working surfaces comprises an outer coating incorporating a release agent such as polytetrafluoroethylene.

It is still another object to provide apparatus and methods including suction into one or both of the rotary transport devices.

Yet another object is to provide apparatus and methods wherein the width direction shrinkage of the web is limited to no more than about 5%, preferably no more than about 1%, most preferably no more than about 0.5%.

SUMMARY OF THE INVENTION

This invention describes methods and apparatus for handling, conveying, transferring, transporting, and the like, a continuous web incorporating stretched elastic-type elements having a retracting force active in the cross-machine direction while maintaining the overall width of the web, thus minimizing shrinkage of the web in the width dimension.

A first family of embodiments of the invention comprises a method of handling a continuous web in a process wherein the web advances in the machine direction, the web having a length defined in the machine direction and a width defined in the cross-machine direction between first and second edges of the web, wherein substrate elements of the web define openings therebetween into the web, and edges of the openings. The method comprises the steps of incorporating into the web stretched elastic-type elements having a retracting force active in the cross-machine direction and urging effective reduction in the width of the web; transporting the web on a first outer working surface of a first rotary transport device, the first outer working surface including a first set of protuberances thereon, the first set of protuberances interacting with the substrate elements defining the edges of a first set of the openings into the web and thereby inhibiting lateral movement of the respective substrate elements defining the edges of the first set of openings, and stabilizing the width of the web in the cross-machine direction between the first and second edges of the web on the first rotary transport device; and transferring the web from the first rotary transport device to a second outer working surface of a second rotary transport device, the second outer working surface including a second set of protuberances thereon, the second set of protuberances interacting with the substrate elements of a second set of the openings into the web and thereby inhibiting lateral movement of the respective edges of the second set of openings, and stabilizing the width of the web in the cross-machine direction between the first and second edges of the web, during the transferring step.

In preferred embodiments, the method includes aligning the first and second outer working surfaces at the locus of closest approach of the first and second outer working surfaces, preferably across the entire width of the web, while transferring the web from the first rotary transport device to the second rotary transport device.

It is also preferred that the first and second rotary transport devices comprise respective first and second substrates, with the substrates comprising respective first and second supports for the respective first and second outer working surfaces, and first and second coatings on the respective first and second substrates, the first and second coatings incorporating the protuberances, and including first and second release agents, preferably comprising polytetrafluoroethylene, in the respective compositions of the first and second coatings.

Preferred methods include drawing suction into one, preferably both, of the first and second rotary transport devices, and thereby assisting in stabilizing the web on the respective rotary transport devices.

The methods of the invention are typically effective to retain the width of the web such that shrinkage in the cross-machine direction, between the first and second edges of the web, during processing of the web on the first and second rotary transport devices, is no more than about 5%, preferably no more than about 1%, most preferably no more than about 0.5%.

In some embodiments, the method includes maintaining a gap between the first and second rotary transport devices at the locus of transferring the web from the first rotary transport device to the second rotary transport device. In other embodiments, the method includes maintaining a nip at the locus of transferring the web from the first rotary transport device to the second rotary transport device, and applying pressure on the nip while transferring the web from the first rotary transport device to the second rotary transport device.

In preferred embodiments, the first and second rotary transport devices have corresponding first and second circumferences, and the first and second sets of protuberances circumscribe the respective circumferences of the first and second rotary/transport devices.

In highly preferred embodiments, the second set of protuberances interacts with the substrate elements defining the edges of the second set of openings into the web adjacent the first and second edges of the web, and thereby inhibits lateral movement of the first and second edges of the web during the transferring step, such that the overall effect of the method is to retain the width of the web such that shrinkage in the cross-machine direction during the transferring step is no more than about 5%.

In typical operation, the sizes of the openings into the web are trivial compared to the width of the web, such that the web comprises a generally uniform structure, and may comprise a porous structure.

In a second family of embodiments, the invention comprehends apparatus for transporting a continuous web in a process wherein the web advances in a machine direction, the web having a length defined in the machine direction and a width defined in the cross-machine direction between first and second edges of the web, wherein substrate elements of the web define openings therebetween into the web, and edges of the openings, the web including therein stretched elastic-type elements having a retracting force active in the cross-machine direction and urging effective reduction in the width of the web, the apparatus comprising a first rotary transport device having a first outer working surface, the first outer working surface including a first set of protuberances thereon, the first set of protuberances being adapted to interact with the substrate elements defining the edges of a first set of the openings into the web and thereby to inhibit lateral movement of the respective edges of the first set of openings, and stabilize the width of the web in the cross-machine direction between the first and second edges of the web on the first rotary transport device; and a second rotary transport device disposed in working relationship with the first rotary transport device to receive a web transferred from the first rotary transport device, and having a second outer working surface, the first and second outer working surfaces being aligned with each other at the locus of closest approach of the first and second outer working surfaces, the second outer working surface including a second set of protuberances thereon, the second set of protuberances being aligned with the first set of protuberances along the direction of advance of the web, and being adapted to interact with the substrate elements defining the edges of a second set of the openings into the web, and thereby to inhibit lateral movement of the respective edges of the second set of openings, and stabilize the width of the web in the cross-machine direction between the first and second edges of the web, during transfer of the web from the first rotary transport device to the second rotary transport device.

Preferably, the first and second outer working surfaces are aligned with each other at the locus of closest approach of the first and second outer working surfaces, across the entire width of the web, for transferring the web from the first rotary transport device to the second rotary transport device.

Also preferably, the first and second rotary transport devices comprise respective first and second substrates comprising respective first and second supports for the respective first and second outer working surfaces, and first and second coatings on the respective first and second substrates, the first and second coatings incorporating the protuberances, and including first and second release agents, preferably including polytetrafluoroethylene, in the respective compositions of the first and second coatings.

One, and preferably both, of the first and second rotary transport devices incorporates suction apparatus therein, thereby to assist in stabilizing the web on the respective rotary transport devices, the overall effect of the apparatus being to retain the width of the web such that in the cross-machine direction, between the first and second edges of the web, is no more than about 5%, preferably no more than about 1%, most preferably no more than about 0.5%.

The apparatus, as set up, preferably includes a gap between the first and second rotary transport devices at the locus of transferring the web from the first rotary transport device to the second rotary transport device. However, the invention does comprehend some embodiments wherein the apparatus incorporates a nip at the locus of transferring the web from the first rotary transport device to the second rotary transport device, and means for applying pressure on the nip while transferring the web from the first rotary transport device to the second rotary transport device.

In some embodiments, the first and second rotary transport devices have corresponding first and second circumferences, and the first and second sets of protuberances circumscribe those respective circumferences.

In typical operating arrangements of the apparatus, the second set of protuberances is adapted to interact with the substrate elements defining the edges of the second set of openings into the web adjacent the first and second edges of the web, thereby to inhibit lateral movement of the first and second edges of the web during transfer of the web from the first rotary transport device to the second rotary transport device, the apparatus being effective to retain the width of the web such that shrinkage of the web in the cross-machine direction, during such transfer is no more than about 5%, preferably no more than about 1%, most preferably no more than about 0.5%.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE ILLUSTRATED EMBODIMENTS

The following detailed description of the illustrated embodiments is made in the context of making panty-type undergarments, and includes apparatus and methods related to processing a web corresponding to one layer of material such as nonwovens and films, preferably two superposed layers of spunbonded polypropylene material, e.g. 0.7 ounce per square yard (osy) each, including performing a plurality of process steps at each of a plurality of registered locations on the web.

The specific context is the production of disposable garments in a continuous combined web containing one or more such layers of material. The garment preforms in the web extend transversely across the width of the web, with the waist portions of the garments extending in the machine direction of the web along or adjacent corresponding opposing side edges of the web. The front and back portions of the garments are on opposing sides of the web. In the embodiments illustrated, the apparatus and methods are concerned with maintaining constant the cross-machine width dimension of the web while the web is being processed through the several processing steps.

Figure 1:
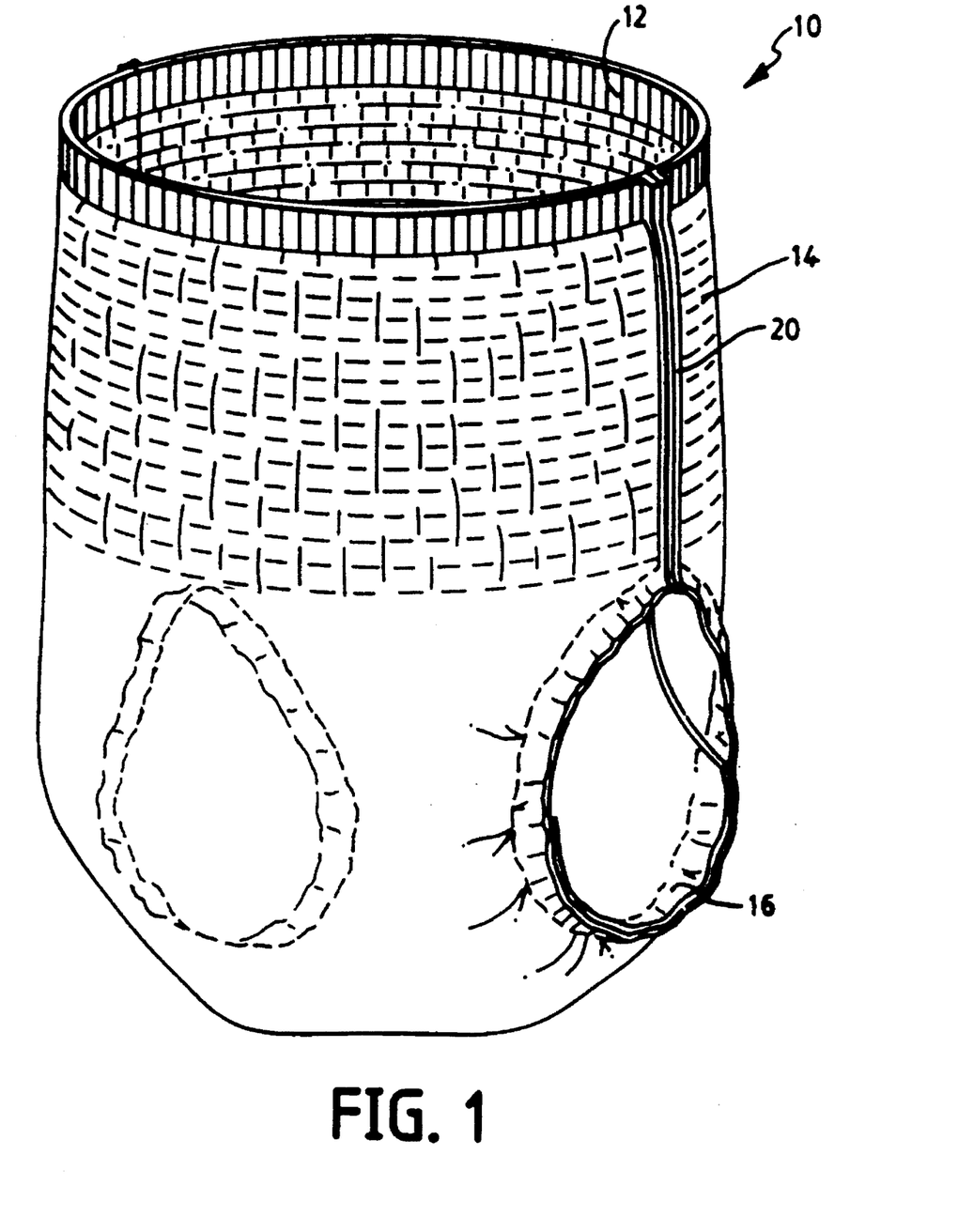
FIG. 1 is a top view of a finished garment which may be made using methods and apparatus of this invention.

It is generally known to make a garment 10 of the type shown in FIG. 1. Such garments typically comprise an assemblage of two or more layers or partial layers of woven or non-woven fabric or films, along with other elements. Elastic may be used at the waist 12, in the body portion 14, and around the leg openings 16.

Figure 2:
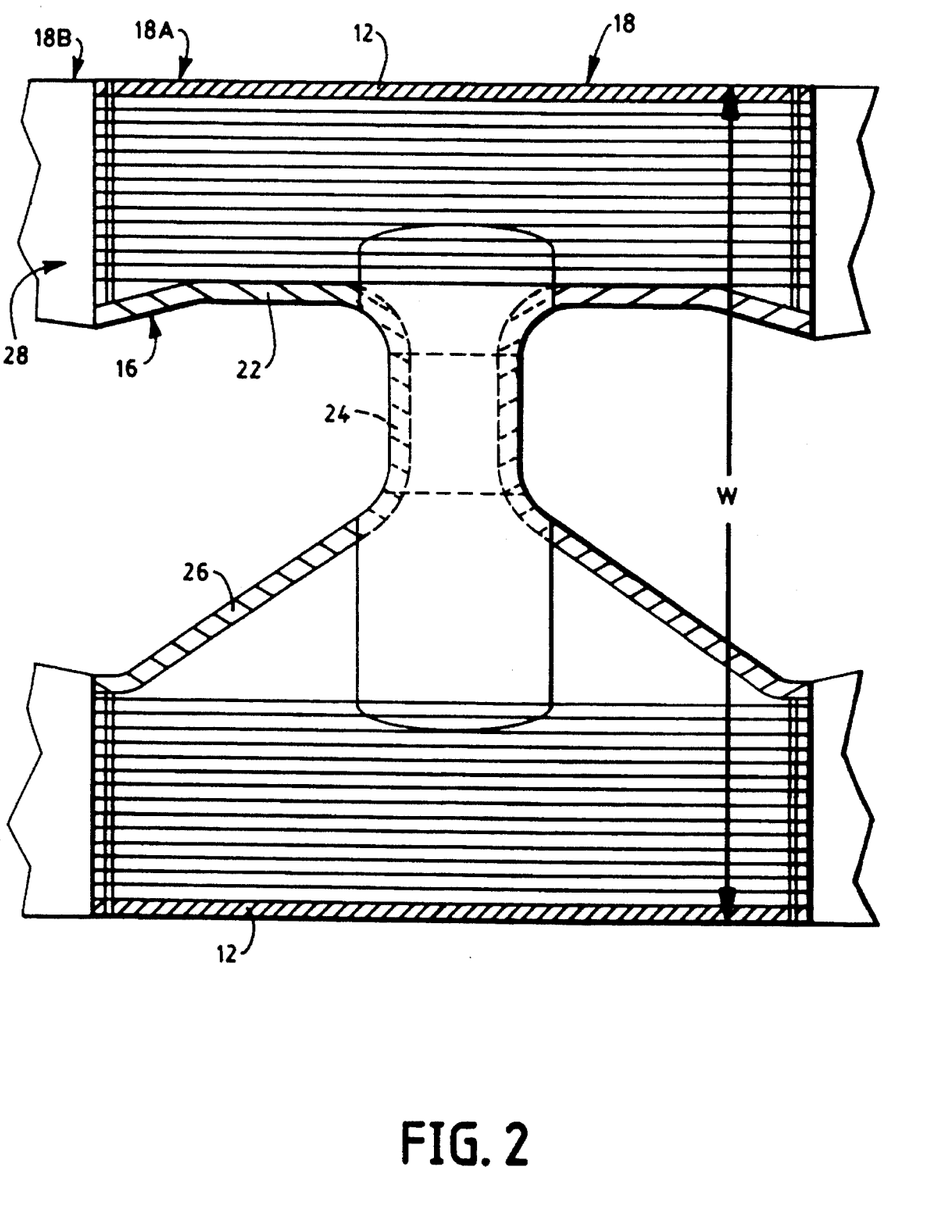
FIG. 2 is a top view of a finished garment blank, as a workpiece in a continuous web, from which the garment of FIG. 1 can be made.

In this context, as in most such processes for fabricating the garment as at 10, a blank 18 such as that shown in FIG. 2 is first made as part of a continuously processed web of material. After the blank is fully fabricated, the sideseams 20 are formed and the garment is severed from the web either as a blank, fully finished or partially finished, or as a fully formed garment article.

The process contemplated by the invention includes forming adjacent leading and trailing blanks 18A and 18B in the web as illustrated in FIG. 2. In the blanks shown, front elastic elements 22, crotch elastic elements 24, and back elastic elements 26 are disposed, in a stretched condition in the web, adjacent the edges of the respective leg openings 16, with the respective stretched elastic elements oriented in directions generally following the contours of the edges of the leg openings 16. Each of such elastic elements 22, 24 and 26 includes one or more segments which extends in a direction transversely across the width dimension "W" of the web (cross-machine direction, or CMD). Such stretched elements, by nature, exert retracting forces active in the cross-machine direction and urge effective reduction in the width "W" of the web.

Figure 3:
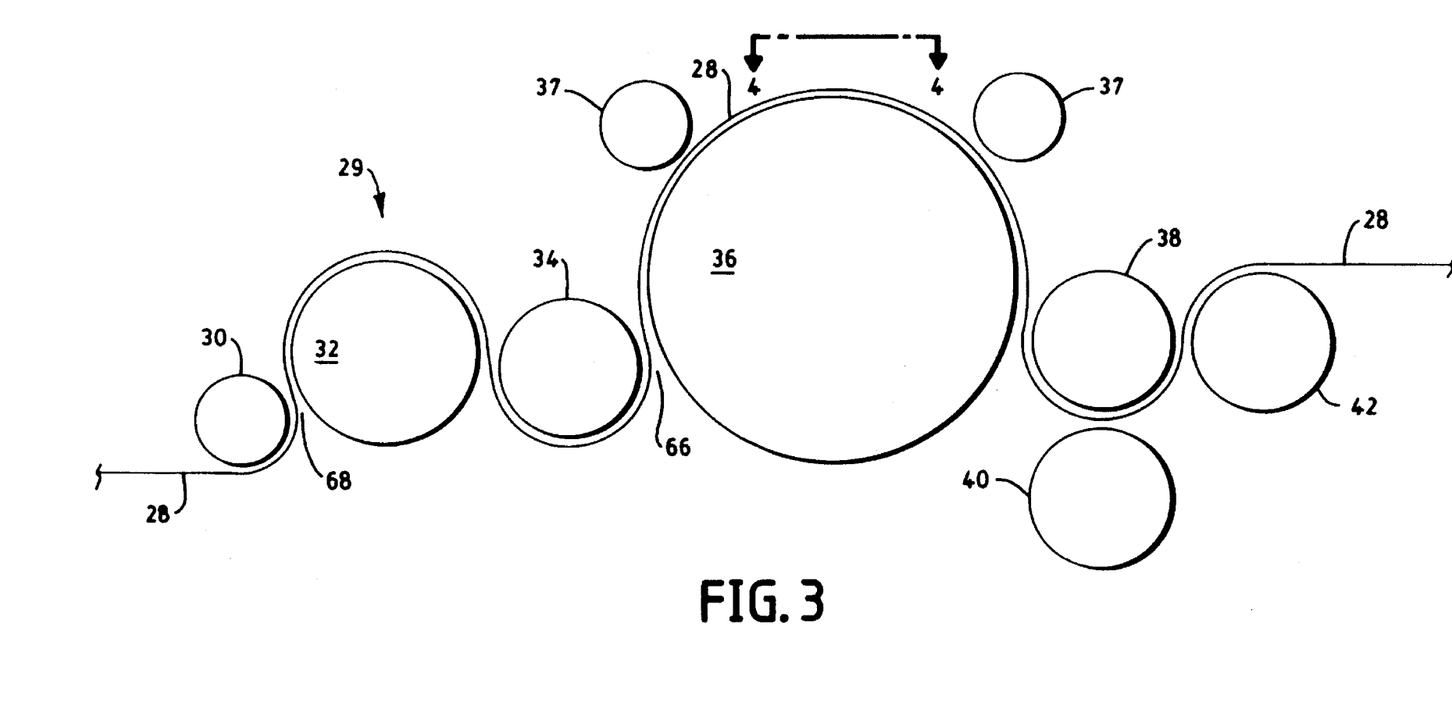
FIG. 3 is a schematic representation of a side elevation view of a portion of a processing line incorporating processing rolls using apparatus and method of the invention.

FIGS. 3–6 illustrate one embodiment of the apparatus and methods of the invention. Referring now to FIG. 3, a continuous web 28 enters the portion 29 of the processing line shown at a first turning roll 30, passing under the turning roll 30 and into a nip 68 between the turning roll 30 and elastic incorporation roll 32. At one or more work stations, not shown, on elastic incorporation roll 32, elastic elements 22, 24 and 26 are incorporated into the web 28 in stretched condition, in the positions they ultimately occupy in blank 18 and garment 10. Typically, the elastic elements are stretched about 100% to about 300% at the time they are incorporated into the web 28.

From the elastic incorporating roll 32, the web 28 passes under a second turning roll 34 and onto the surface of construction roll 36. At one or more work stations 37 generally represented as rolls on construction roll 36, additional work is done on web 28 in fabricating blanks, in serial fashion along the generally endless length of web 28, such that a series of blanks 18, or blank pre-forms, are fabricated in the web 28, one following the other, generally as shown at 18A and 18B in FIG. 2.

From construction roll 36, the web 28 passes under anvil roll 38, and between anvil roll 38 and cutter roll 40. From anvil roll 38, web 28 passes over third turning roll 42 and on to further processing beyond the scope of this invention.

Still referring to FIG. 3, the elastic elements 22, 24, and 26 exert retractive forces in the web 28, in the cross-machine direction, beginning at the elastic incorporation roll 32, and all along the web for the remainder of the length of the portion of the processing system illustrated in FIG. 3, including through the work stations 37. Work performed at work stations 37, and at anvil roll 38, requires registration of each blank pre-form with the working elements at the respective work station. Accordingly, the web dimensions should be stable, both the length dimension of the web and the width dimension of the web, through the processing operation represented by the portion 29 of the processing line.

Figure 4:
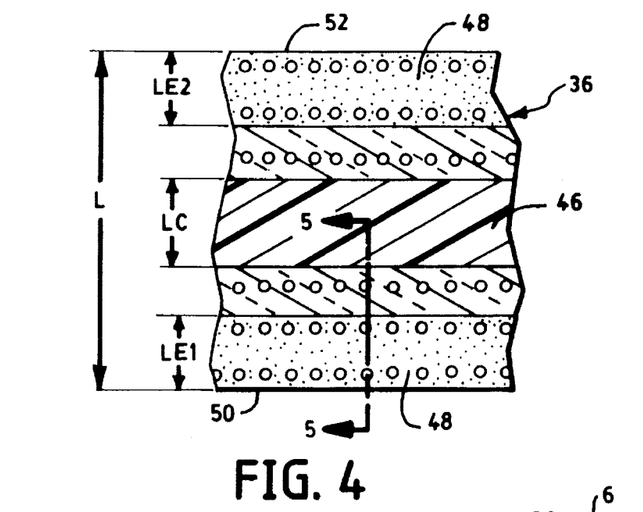
FIG. 4 is a top view of a fragment of one of the processing rolls, taken at 4—4 of FIG. 3.
Figure 5:
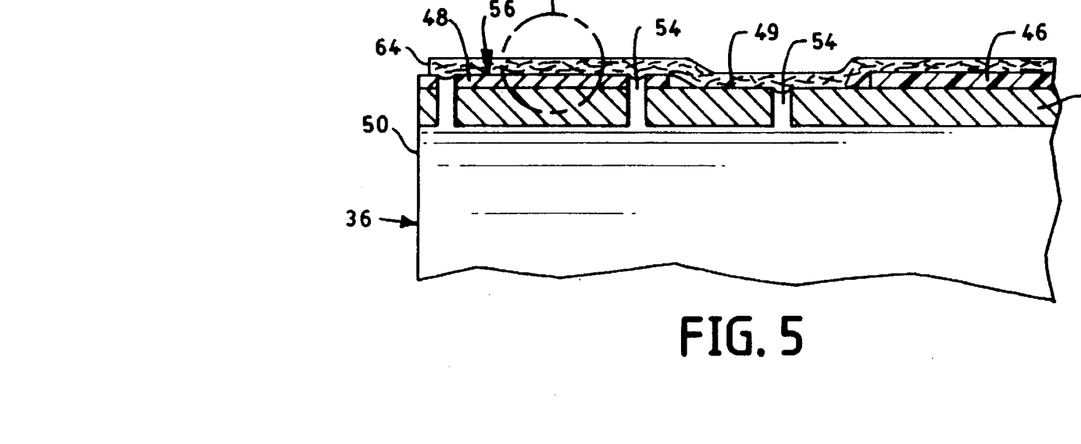
FIG. 5 is a fragmentary cross-section of a process roll, showing a representative coating applied to rolls of the invention, and incorporating protuberances therein, taken at 5—5 of FIG. 4.
Figure 6:
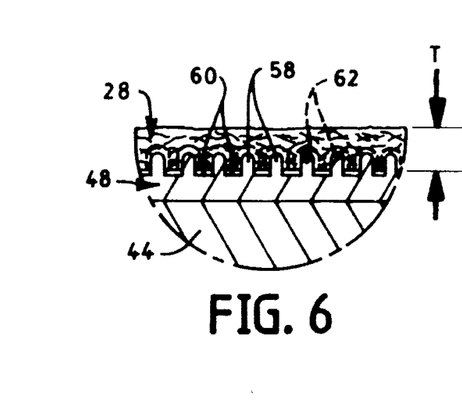
FIG. 6 is an enlarged cross-section of a portion of the roll of FIG. 5, taken at the broken circle 6 in FIG. 5.

Referring to FIGS. 4–6, the outer circumference of the construction roll 36 generally includes a substrate 44 which extends entirely about the circumference of the construction roll, and along the entire length "L" of the roll, which corresponds generally with the width "W" of the web 28.

A first coating 46 comprising rubber or like resilient material extends entirely about the circumference of the construction roll 36 and along only a central portion "LC" of the length of the roll.

A second coating 48 has a composition incorporating primarily metallic elements. Coating 48 extends entirely about the circumference of the construction roll, and along first and second portions "LE1" and "LE2" of the length "L" of the construction roll, adjacent the first and second ends 50 and 52 of the roll.

Referring to FIGS. 4 and 5, a series of suction ports 54 communicate suction from inside the construction roll 36, urging the web 28 firmly against the composite of the outer working surface 56 of the roll 36, the composite of the outer working surface including the coatings 46 and 48, as well as uncoated portions 49 of the outer surface of the substrate 44.

Referring to FIG. 6, the second coating 48 is preferably applied as a generally metallic composition, by plasma or other high temperature application process. For example, coating 48 may be applied as a plasma spray, or using an electric arc medium. Such coatings are available from Plasma Coatings Inc., Waterbury, Conn. A preferred such coating is available from Plasma Coatings Inc. under the designation of product number 936.

Using the application processes above mentioned, the resulting coating 48 is characterized by an irregular surface texture, including protuberances 58 spaced about the coating surface at random, though closely spaced, locations. Depending on the method of application used, and the exact composition used, the surface of coating 48 may resemble the working surface of conventional sandpaper. The roughened surface comprising an array of protrusions extending outwardly at least about 0.006 mm preferably up to about 3 mm, more preferably between about 0.01 mm and about 0.03 mm. In some applications, as in the instant application to holding a continuous web dimensionally stable during transfer from one roll to another, the surface of the coating 48 need not be so aggressive, and so appears more like the working surface of dull, or used, sandpaper.

In combination with the protuberances 58, the surface of coating 48 correspondingly includes valleys 60 about the respective protuberances.

The exact nature of any particular metal-based coating 48 depends somewhat on the composition used, and the method of applying it. Accordingly, the protuberances of the applied coating may be characterized as quite aggressive, like fresh sandpaper, or may be more muted, like used sandpaper. The coating 48 may incorporate therein one or more agents to assist the release of the web from the working surface, such as polytetrafluoroethylene, commonly sold under the trade name Teflon® by the DuPont de Nemours Corporation, Wilmington, Del.

In the application at hand, the web 28, as it enters the process depicted at turning roll 30, can be generally represented as a conventional porous spunbonded polypropylene nonwoven, 0.7 ounces per square yard, having a generally entangled mat of polypropylene fibers. Additional layers of like material may be added to the web 28 as it progresses through the several processing steps.

FIG. 6 illustrates that, as the web 28 is urged against coating 48, e.g. by normal tension in the web or by suction drawn by the respective rolls 32, 34, 36, or 38, the protuberances 58 project into the web at existing openings in the spunbonded web between the fibers. As the protuberances enter the web under the urging of suction or the longitudinal tension in the web, they expand existing spaces between the fibers, to create a first set of expanded openings 62 having edges, with fiber elements of the web being disposed at those edges, in engagement with the protuberances.

While protuberances 58 may extend entirely through the web, such is generally not the case and is not necessary. By extending substantially into the thickness "T" of the web as shown in FIG. 6, the protuberances engage the fibers of the web about generally the entire area of the web overlying the area coated with coating 48, with sufficient engagement that the web is held dimensionally stable, against especially the retractive forces of the elastic as applied in the cross-machine direction. As seen in FIG. 4, the coating 48 extends to the ends 50 and 52 of the construction roll 36, such that the edges 64 of the web 28 are underlain with coating 48. Correspondingly, the respective protuberances 58 underlying the web at edges 64 engage the web at even the outer extremities of edges 64, thereby to hold the web dimensionally stable against the width dimension retractive forces being exerted by the elastic elements 22, 24, and 26, even at edges 64.

Figure 7:
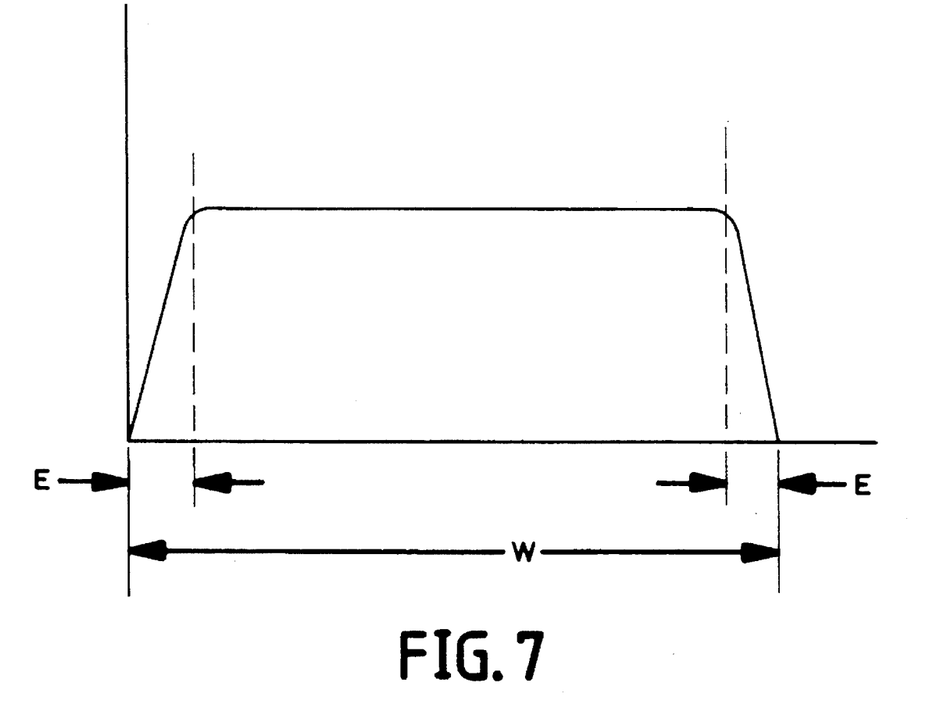
FIG. 7 is a graphical representation of the effective downward force on the web across the width of the web.

FIG. 7 represents the effective downward pressure on a web across its width "W," and therefore the effective ability of that downward pressure to hold the web dimensionally stable against lateral forces in the web tending to destabilize the web in the width dimension.

At each edge 64 of the web, the net downward pressure on the web goes from a general maximum pressure, represented by the flat portion of the curve across the middle of the width "W," to zero at the outer extremities of the web. The transition from the general maximum pressure to zero pressure is represented as the transition zone labelled "E."

The width of the transition zone "E" depends on the ability of the coating 48, in combination with the suction if any, to immobilize the edges 64 of the web in the width, or CMD, dimension of the web. Using the specific coating 48 described above, with the web described above, in combination with auction of about 0 to about 80 inches of water, preferably about 5 to about 15 inches, more preferably about 10 inches of water, the reduction in width associated with the transition zone is limited to less than about 5%. If a less aggressive coating 48 is used, or if the suction is reduced, the reduction in width associated with the transition zones increases, to the point where, without use of the coating 48, the reduction in width may be substantially greater than about 5%.

In the portion 29 of the processing line shown, all rolls which transport the web after the elastics 22, 24, and 26 have been incorporated in the web have a coating 48 effective to maintain the CMD dimensional stability in the web while the web is being transported on the respective roll. All rolls also preferably include suction to assist the coating 48 in holding the web. Thus at least rolls 32, 34, 36, 38, and 42 have a coating 48.

The web can be effectively held without any use of suction. However, use of suction minimizes the shrinkage in width, thus use of suction on each of the rolls is preferred.

In addition, the inventors have found that the web can traverse a gap 66 as shown in FIG. 3 between rolls while still maintaining the dimensional stability of the web, so long as both rolls incorporate a coating 48 suitable to engage especially the edges 64 of the web. By contrast, the rolls can be satisfactorily engaged at a conventional nip, with corresponding conventional amounts of pressure for e.g. transferring the web 28 from one roll to another.

Since the protuberances 58 are randomly spaced in the coating 48, the coating on each roll engages its own unique set of existing openings in the web to thereby create its own set of expanded openings 62 while engaged with the fibers of the web.

While not absolutely necessary, the effectiveness of maintaining dimensional stability in the web is somewhat enhanced where the outer working surfaces 56 of respective rolls transferring and receiving the web are aligned with each other across the entire width of the web.

The inventors have found that by using a coating 48 including the polytetrafluoroethylene in its composition, adhesive and the like normally aggressively adhering materials can be easily cleaned from the surface of coating 48 without sacrificing the ability of the coating 48 to hold the web 28 and thereby to maintain the dimensional stability of the web.

It is contemplated that the operation and functions of the invention have become fully apparent from the foregoing description of elements, but for completeness of disclosure, the usage of the invention will be briefly described.

A web 28 enters the processing operation illustrated in FIG. 3 at turning roll 30, and is pressed against the elastic incorporating roll 32 at nip 68. As the web is transported on roll 32, threads of elastic (not shown) are incorporated into the web at locations properly positioned to provide the elastic properties desired in the finished product, namely the garment article 10.

Once the elastics have been incorporated in the web on roll 32, the web includes elements having retracting forces active in the cross-machine direction and urging effective reduction in the width of the web.

From the elastic incorporating roll 32, the web 28 is transferred to turning roll 34, and from turning roll 34 to construction roll 36. On construction roll 36, further work is done on the web at the work stations represented schematically as 37. From construction roll 36, the web is transferred to anvil roll 38. Leg openings 16 are cut by cutter roll 40, against anvil roll 38. The web then passes over turning 42, and passes out of the portion 29 of the processing line of interest in this invention.

Having thus described the invention in full detail, it will be readily apparent that various changes and modifications may be made without departing from the spirit of the invention. All such changes and modifications are contemplated as being within the scope of the present invention, as defined by the following claims.

What is claimed is:

1. A method of handling a continuous web in a process wherein the web advances in a machine direction, the web having a length defined in the machine direction and a width defined in the cross-machine direction between first and second edges of the web, wherein substrate elements of the web define openings therebetween into the web, and edges of the openings, the method comprising the steps of:

(a) incorporating into the web stretched elastic-type elements having a retracting force active in the cross-machine direction and urging effective reduction in the width of the web;

(b) transporting the web on a first outer working surface of a first rotary transport device, the first outer working surface including a first set of protuberances thereon, the first set of protuberances interacting with the substrate elements defining the edges of a first set of the openings into the web and thereby inhibiting lateral movement of the respective substrate elements defining the edges of the first set of openings, and stabilizing the width of the web in the cross-machine direction between the first and second edges of the web on the first rotary transport device; and (c) transferring the web from the first rotary transport device to a second outer working surface of a second rotary transport device, the second outer working surface including a second set of protuberances thereon, the second set of protuberances interacting with the substrate elements of a second set of the openings into the web and thereby inhibiting lateral movement of the respective edges of the second set of openings, and stabilizing the width of the web in the cross-machine direction between the first and second edges of the web, during the transferring step.

2. A method as in claim 1, including aligning the first and second outer working surfaces at the locus of closest approach of the first and second outer working surfaces while transferring the web from the first rotary transport device to the second rotary transport device.

3. A method as in claim 1, including aligning the first and second outer working surfaces at a locus of closest approach of the first and second outer working surfaces, across the entire width of the web, while transferring the web from the first rotary transport device to the second rotary transport device.

4. A method as in claim 1, the first rotary transport device comprising a substrate supporting the first outer working surface, and a coating on the substrate, incorporating the first set of protuberances, and including a release agent in the composition of the coating.

5. A method as in claim 4 including incorporating polytetrafluoroethylene as said release agent.

6. A method as in claim 1, the first and second rotary transport devices comprising respective first and second substrates comprising respective first and second supports for the respective first and second outer working surfaces, and first and second coatings on the respective first and second substrates, the first and second coatings incorporating the protuberances, and including first and second release agents in the respective compositions of the first and second coatings.

7. A method as in claim 6 including incorporating polytetrafluoroethylene as said first and second release agents.

8. A method as in claim 1, and including drawing suction into one of the first and second rotary transport devices, and thereby assisting in stabilizing the web on the respective rotary transport device.

9. A method as in claim 1, and including drawing suction into both of the first and second rotary transport devices, and thereby assisting in stabilizing the web on the first and second rotary transport devices.

10. A method as in claim 1, the method being effective to retain the width of the web dimensionally stable such that shrinkage in the cross-machine direction, between the first and second edges of the web, is no more than about 5%.

11. A method as in claim 8, the method being effective to retain the width of the web dimensonally stable such that shrinkage in the cross-machine direction, between the first and second edges of the web, is no more than about 5%.

12. A method as in claim 11, the method being effective to retain the width of the web dimensionally stable such that shrinkage in the cross-machine direction, between the first and second edges of the web, is no more than about 1%.

13. A method as in claim 12, the method being effective to retain the width of the web dimensionally stable such that shrinkage in the cross-machine direction, between the first and second edges of the web, is no more than about 0.5%.

14. A method as in claim 9, the method being effective to retain the width of the web dimensionally stable such that shrinkage in the cross-machine direction, between the first and second edges of the web, is no more than about 5%.

15. A method as in claim 14, the method being effective to retain the width of the web dimensionally stable such that shrinkage in the cross-machine direction, between the first and second edges of the web, is no more than about 1%.

16. A method as in claim 15, the method being effective to retain the width of the web dimensionally stable such that shrinkage in the cross-machine direction, between the first and second edges of the web, is no more than about 0.5%.

17. A method as in claim 1, including maintaining a gap between the first and second rotary transport devices at a locus of transferring the web from the first rotary transport device to the second rotary transport device.

18. A method as in claim 1, including maintaining a nip at a locus of transferring the web from the first rotary transport device to the second rotary transport device, and applying pressure on the nip while transferring the web from the first rotary transport device to the second rotary transport device.

19. A method as in claim 1, the first and second rotary transport devices having corresponding first and second circumferences, the first and second sets of protuberances circumscribing the respective circumferences of the first and second rotary transport devices.

20. A method as in claim 1, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 5%.

21. A method as in claim 9, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 5%.

22. A method as in claim 21, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 1%.

23. A method as in claim 22, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 0.5%.

24. A method as in claim 8, the first rotary transport device comprising a substrate supporting the first outer working surface, and a coating on the substrate, incorporating the first set of protuberances, and including a release agent in the composition of the coating.

25. A method as in claim 24 including incorporating polytetrafluoroethylene as said release agent.

26. A method as in claim 9, the first and second rotary transport devices comprising respective first and second substrates comprising respective first and second supports for the respective first and second outer working surfaces, and first and second coatings on the respective first and second substrates, the first and second coatings incorporating the protuberances, and including first and second release agents in the respective compositions of the first and second coatings.

27. A method as in claim 26 including incorporating polytetrafluoroethylene as said first and second release agents.

28. A method as in claim 17, and including drawing suction into one of the first and second rotary transport devices, and thereby assisting in stabilizing the web on the respective rotary transport device.

29. A method as in claim 28, the method being effective to retain the width of the web dimensionally stable such that shrinkage in the cross-machine direction, between the first and second edges of the web, is no more than about 5%.

30. A method as in claim 29, the method being effective to retain the width of the web dimensionally stable such that shrinkage in the cross-machine direction, between the first and second edges of the web, is no more than about 1%.

31. A method as in claim 30, the method being effective to retain the width of the web dimensionally stable such that shrinkage in the cross-machine direction, between the first and second edges of the web, is no more than about 0.5%.

32. A method as in claim 1, the sizes of the openings into the web being trivial compared to the width of the web, such that the web comprises a generally uniform structure.

33. A method as in claim 1, said first and second outer surfaces being defined by corresponding first and second outer coatings on said first and second rotary transport devices, said first and second outer coatings comprising compositions incorporating primarily metallic elements, adapted to cutting operations.

34. A method of transporting a continuous web in a process wherein the web advances in a machine direction, the web having a length defined in the machine direction and a width defined in the cross-machine direction between first and second edges of the web, wherein substrate elements of the web define openings therebetween into the web, and edges of the openings, the web including therein stretched elastic-type elements having a retracting force active in the cross-machine direction and urging effective reduction in the width of the web, the method comprising the steps of:

(a) transporting the web on a first outer working surface of a first rotary transport device, the first outer working surface including a first set of protuberances thereon, the first set of protuberances interacting with the substrate elements defining the edges of a first set of the openings into the web and thereby inhibiting lateral movement of the respective edges of the first set of openings, and stabilizing the width of the web in the cross-machine direction between the first and second edges of the web on the first rotary transport device; and (b) transferring the web from the first rotary transport device to a second outer working surface of a second rotary transport device, the first and second outer working surfaces being aligned with each other at a locus of closest approach of the first and second outer working surfaces, the second outer working surface including a second set of protuberances thereon, the second set of protuberances being aligned with the first set of protuberances along the direction of advance of the web, and interacting with the substrate elements defining the edges of a second set of the openings into the web, and thereby inhibiting lateral movement of the respective edges of the second set of openings, and stabilizing the width of the web in the cross-machine direction between the first and second edges of the web, during the transferring step.

35. A method as in claim 34, including aligning the first and second outer working surfaces at the locus of closest approach of the first and second outer working surfaces, across the entire width of the web, while transferring the web from the first rotary transport device to the second rotary transport device.

36. A method as in claim 34, the first rotary transport device comprising a substrate comprising a support for the first outer working surface, and a coating on the substrate, incorporating the first set of protuberances, and including a release agent in the composition of the coating.

37. A method as in claim 36 including incorporating polytetrafluoroethylene as said release agent.

38. A method as in claim 34, the first and second rotary transport devices comprising respective first and second substrates comprising respective first and second supports for the respective first and second outer working surfaces, and first and second coatings on the respective first and second substrates, the first and second coatings incorporating the protuberances, and including first and second release agents in the respective compositions of the first and second coatings.

39. A method as in claim 38 including incorporating polytetrafluoroethylene as said first and second release agents.

40. A method as in claim 34, and including drawing suction into one of the first and second rotary transport devices, and thereby assisting in stabilizing the web on the respective rotary transport device.

41. A method as in claim 34, and including drawing suction into both of the first and second rotary transport devices, and thereby assisting in stabilizing the web on the first and second rotary transport devices.

42. A method as in claim 34, the method being effective to retain the width of the web dimensionally stable such that shrinkage in the cross-machine direction, between the first and second edges of the web, is no more than about 5%.

43. A method as in claim 40, the method being effective to retain the width of the web dimensionally stable such that shrinkage in the cross-machine direction, between the first and second edges of the web, is no more than about 5%.

44. A method as in claim 43, the method being effective to retain the width of the web dimensionally stable such that shrinkage in the cross-machine direction, between the first and second edges of the web, is no more than about 1%.

45. A method as in claim 44, the method being effective to retain the width of the web dimensionally stable such that shrinkage in the cross-machine direction, between the first and second edges of the web, is no more than about 0.5%.

46. A method as in claim 41, the method being effective to retain the width of the web dimensionally stable such that shrinkage in the cross-machine direction, between the first and second edges of the web, is no more than about 5%.

47. A method as in claim 46, the method being effective to retain the width of the web dimensionally stable such that shrinkage in the cross-machine direction, between the first and second edges of the web, is no more than about 1%.

48. A method as in claim 47, the method being effective to retain the width of the web dimensionally stable such that shrinkage in the cross-machine direction, between the first and second edges of the web, is no more than about 0.5%.

49. A method as in claim 34, including maintaining a gap between the first and second rotary transport devices at the locus of transferring the web from the first rotary transport device to the second rotary transport device.

50. A method as in claim 34, including maintaining a nip at the locus of transferring the web from the first rotary transport device to the second rotary transport device, and applying pressure on the nip while transferring the web from the first rotary transport device to the second rotary transport device.

51. A method as in claim 34, the first and second rotary transport devices having corresponding first and second circumferences, the first and second sets of protuberances circumscribing the respective circumferences of the first and second rotary transport devices.

52. A method as in claim 34, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 5%.

53. A method as in claim 52, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 1%.

54. A method as in claim 53, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 0.5%.

55. A method as in claim 41, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 5%.

56. A method as in claim 55, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 1%.

57. A method as in claim 56, the second set of protuberances interacting with the substrate elements defining the edges of the second set of openings into the web adjacent the first and second edges of the web, and thereby inhibiting lateral movement of the first and second edges of the web during the transferring step, the method being effective to retain the width of the web dimensionally stable such that shrinkage in the cross-machine direction during the transferring step is no more than about 0.5%.

58. A method as in claim 40, the first rotary transport device comprising a substrate supporting the first outer working surface, and a coating on the substrate, incorporating the first set of protuberances, and including a release agent in the composition of the coating.

59. A method as in claim 58 including incorporating polytetrafluoroethylene as said release agent.

60. A method as in claim 41, the first and second rotary transport devices comprising respective first and second substrates comprising respective first and second supports for the respective first and second outer working surfaces, and first and second coatings on the respective first and second substrates, the first and second coatings incorporating the protuberances, and including first and second release agents in the respective compositions of the first and second coatings.

61. A method as in claim 60 including incorporating polytetrafluoroethylene as said first and second release agents.

62. A method as in claim 49, and including drawing suction into one of the first and second rotary transport devices, and thereby assisting in stabilizing the web on the respective rotary transport device.

63. A method as in claim 62, the method being effective to retain the width of the web dimensionally stable such that shrinkage in the cross-machine direction, between the first and second edges of the web, is no more than about 5%.

64. A method as in claim 63, the method being effective to retain the width of the web dimensionally stable such that shrinkage in the cross-machine direction, between the first and second edges of the web, is no more than about 1%.

65. A method as in claim 64, the method being effective to retain the width of the web dimensionally stable such that shrinkage in the cross-machine direction, between the first and second edges of the web, is no more than about 0.5%.

66. A method as in claim 34, the sizes of the openings into the web being trivial compared to the width of the web, such that the web comprises a generally uniform structure.

67. A method as in claim 34, said first and second outer surfaces being defined by corresponding first and second outer coatings on said first and second rotary transport devices, said first and second outer coatings comprising compositions incorporating primarily metallic elements, adapted to cutting operations.

\* \* \* \* \*